US00PP15563P2

(12) United States Plant Patent
Brits

(10) Patent No.: US PP15,563 P2
(45) Date of Patent: Feb. 15, 2005

(54) ***PLECTRANTHUS* PLANT NAMED 'K111201'**

(50) Latin Name: *Plectranthus hybrida*
Varietal Denomination: K111201

(76) Inventor: Gert Johannes Brits, 28, Flamingo Road, ZA-7600 Stellenbosch (ZA)

( * ) Notice: Subject to any disclaimer, the term of this patent is extended or adjusted under 35 U.S.C. 154(b) by 0 days.

(21) Appl. No.: 10/716,598

(22) Filed: Nov. 20, 2003

(51) Int. Cl.[7] ..... A01H 5/00

(52) U.S. Cl. ..... Plt./263

(58) Field of Search ..... Plt./373, 263

*Primary Examiner*—Anne Marie Grunberg
*Assistant Examiner*—June Hwu
(74) *Attorney, Agent, or Firm*—Foley & Lardner, LLP

(57) ABSTRACT

A new and distinct cultivar of *Plectranthus* plant named 'K111201', characterized by having more compact, freely branching plant habit; shorter production time; vigorous growth habit; large almost white flowers; upright main lip of corolla; and shiny green foliage.

3 Drawing Sheets

Latin name of genus and species of the plant claimed: *Plectranthus hybrida.*
Variety denomination: K111201.

BACKGROUND OF THE INVENTION

The present invention relates to a new and distinct cultivar of *Plectranthus* plant, botanically known as *Plectranthus hybrida* (Family Lamiaceae), hereinafter referred to by the name 'K111201'.

The new *Plectranthus,* 'K111201', is a new and distinct mutation (sport), detected in a production batch of *Plectranthus hybrida,* 'P000603' (U.S. Plant patent application Ser. No. 10/716,659) by the Inventor, Gert Johannes Brits, in Kortegaard, Nörre Söby, Denmark. The objective of the breeding program in which the mutation was detected is to improve upon the *Plectranthus* varieties currently available, such as the cultivar 'Edelbau' (unpatented), by developing a *Plectranthus* variety with a more compact growth habit, larger flowers and improved vigor. The new cultivar has been produced only by vegetative propagation (cuttings). The Inventor selected the new *Plectranthus* cultivar on the basis of its compact growth habit, larger flowers and increased vigor.

Asexual reproduction of the new cultivar by terminal cuttings taken and propagated, has shown that each of the progenies exhibit characteristics identical to the original plant. These characteristics have been shown to come true to form through many generations of asexual propagation under commercial production conditions in Nr. Lyndelse, Fyn, Denmark. The present invention has been tested under lighted greenhouse conditions and for keeping quality in a consumer environment, but may differ in various aspects if grown under different conditions.

SUMMARY OF THE INVENTION

Plants of the cultivar 'K111201' have not been observed under all possible environmental conditions. The phenotype may vary somewhat with variations in environment such as temperature, light intensity, day length, and fertility level without, however, any variance in genotype.

The following traits have been repeatedly observed and are determined to be the unique characteristics of 'K111201'. These characteristics in combination distinguish 'K111201' as a new and distinct cultivar:

1. White flowers with purple spots, upright corolla lip;
2. Compact and freely branching plant habit;
3. Shorter production time, 14 weeks compared to the typical 16 weeks; and
4. Shiny green foliage.

Side-by-side comparisons between the instant plant and the "mother" cultivar 'P000603' were conducted by the Inventor. Plants of 'K111201' differ from 'P000603' in the following characteristics:

1. Plants of 'K111201' have larger, almost white flowers with pink to purple spots, while plants of 'P000603' have slightly smaller pink flowers.
2. Plants of 'K111201' have better branching growth habit and shiner foliage than plants of 'P000603'.
3. Plants of 'K111201' have a faster growth rate than plants of 'P000603'.
4. Plants of 'K111201' have an upright main lip of corolla.

BRIEF DESCRIPTION OF THE DRAWINGS

The accompanying photographic drawings illustrate the overall appearance of the new cultivar, showing the colors as true as it is reasonably possible to obtain in colored reproductions of this type. Colors in the photographs may differ slightly from the color values cited in the detailed botanical description, which more accurately describe the actual colors of 'K111201'.

The first photographic drawing shows a side perspective view of a typical flowering plant of 'K111201' in its entirety as grown in 12 cm pots.

The second photographic drawing shows a close-up view of the inflorescence of 'K111201'.

The third photographic drawing shows a close-up view of typical flowering racemes of 'K111201'.

DETAILED BOTANICAL DESCRIPTION

In the following description, color references are made to The Royal Horticultural Society (R.H.S.) Colour Chart, $4^{th}$ edition. Plants were grown under greenhouse conditions.

The plants described were between 15 and 18 weeks old after cutting, as grown in 12 cm pots.

Parentage: Sport mutation discovered in a production batch of *Plectranthus hybrida,* 'P000603', a hybrid backcross between proprietary selection of *Plectranthus* named 'F1' (unpatented) and unnamed *Plectranthus hilliardiae* (unpatented).

Propagation:

*Type cutting.*—Terminal vegetative cuttings.

Plant description:

*Form.*—Perennial, herbaceous plant with upright, branched plant form.

*Crop time.*—Flowering induced by short day treatment in 12 cm pots for 4 weeks under greenhouse conditions.

*Plant height* (*soil level to top of plant plane*).—About 20 cm.

*Plant spread.*—About 20 cm.

*Stem.*—Upright, stiff, square, branching from base, RHS 141 B (gray green).

*Vigor.*—Vigorous growth rate.

*Foliage description.*—Leaves single, ovate, serrate. Arrangement: opposite, decussate. Length: 7 cm. Width: 5 cm. Apex: Acuminate. Base: Cuneate. Texture: adaxial: rough (hispid), shiny; abaxial: smooth, velvety. Venation: prominent, green, RHS 138 A. Color, ventral side: Young foliage, upper and lower surfaces: RHS 136 A, green. Mature foliage, upper and lower surfaces: RHS 136 A. Color, dorsal side: Young foliage, RHS 139 C. Mature foliage: RHS 136 A.

*Petiole.*—2 cm in length, 2 mm diameter; hispid texture, RHS 138 A.

Flower description:

*Flower arrangement.*—Raceme of panicles.

*Flower shape.*—Irregular labiate, flat tubular with 4 lips of different size and shape.

*Flower longevity on the plant.*—Longevity of individual flowers is highly dependent on temperature and light conditions; single flowers last 4 to 6 days in greenhouse conditions with full sun and temperatures not exceeding 20° C. 'K111201' may retain flowers up to 4 weeks with sufficient sunlight and temperatures not exceeding 20° C.

*Number of flowers per inflorescence.*—20; 60 per stem; up to 150 per plant.

*Inflorescence size.*—Length (average): 8 cm; Diameter: 6 cm. individual flower 25 mm vertical diameter, 9 mm horizontal diameter.

*Floral tube.*—Length 23 mm; Diameter (average): 5.5 mm.

*Buds.*—Length: Up to 12 mm before antithesis; height: 5 mm; width: 1 mm; tubular with angular "head", RHS 145 C; base RHS 145 D to white, closest to RHS 155D.

*Petals.*—5 fused to basal, flat tubular corolla. Lips spotted, velvety texture. Top lip (2 fused) to inverted cordate form, revolute upright, 12 mm. Bottom lip involute, almost cup-shaped, 7 mm. Wing lips small, rounded, 4 mm. Color: ventral side of lips: whiter than RHS 155 D; spots: violet, RHS 84 A; throat: white, RHS 155 D; dorsal side: white, RHS 155 C.

*Sepals.*—5, basally fused, 2 mm in length, 1 mm in width, immature and mature color RHS 138B, both upper and lower surfaces.

*Calyx.*—5 pointed lobes fused at base; veins: green, RHS 138 B.

*Pedicel.*—6 mm length, 1 mm diameter, color RHS 138A.

*Peduncle.*—6 mm length, 3 mm diameter, color RHS 138 A.

Reproductive organs:

*Stamen.*—4 monoadelphous, lower part fused to corolla tube.

*Anther.*—Kidney-shaped, purple, N79B; 0.25 mm; filament 6 mm.

*Pistil.*—1, lower part fused to corolla tube; free part 5 mm, curling upward with cleft stigma, purple, N79B.

*Ovary.*—N144A, yellow-green.

*Seed.*—5 in quantity, 1 mm length, 1 mm diameter, color of immature seed RHS 150B.

Fragrance: None.

Weather tolerance: Plants of the new *Plectranthus* have exhibited good tolerance to drought, rain and wind, low temperature resistant to 5° C.

I claim:

1. A new and distinct cultivar of *Plectranthus* plant named 'K111201', as illustrated and described herein.

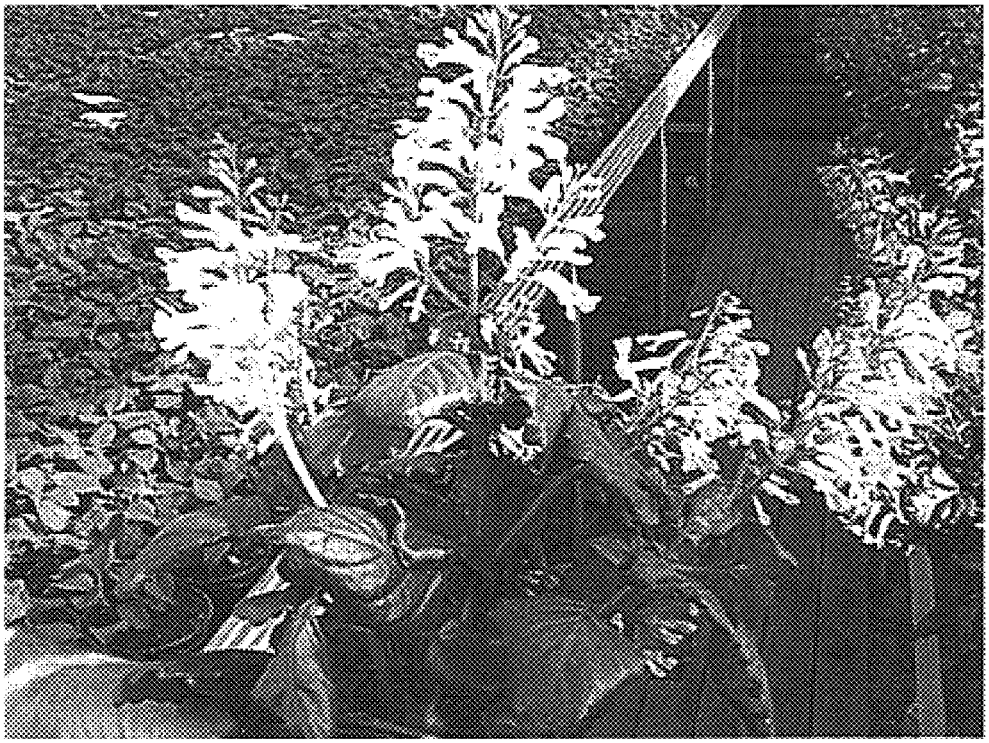

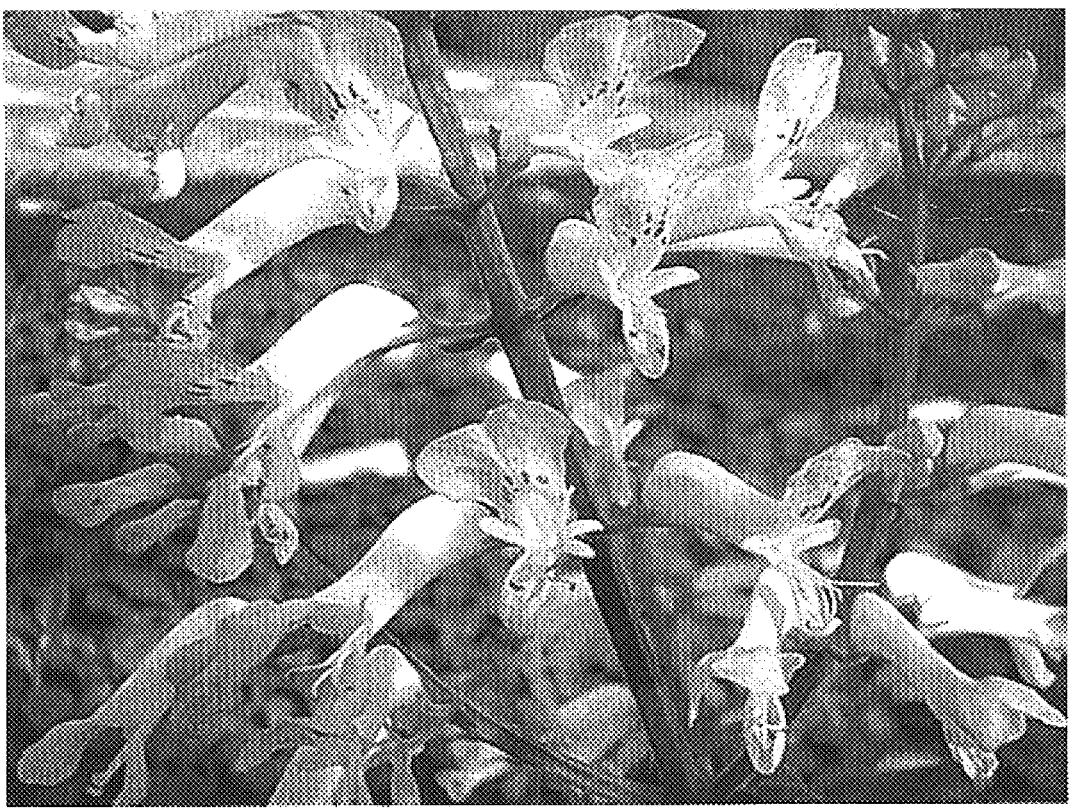

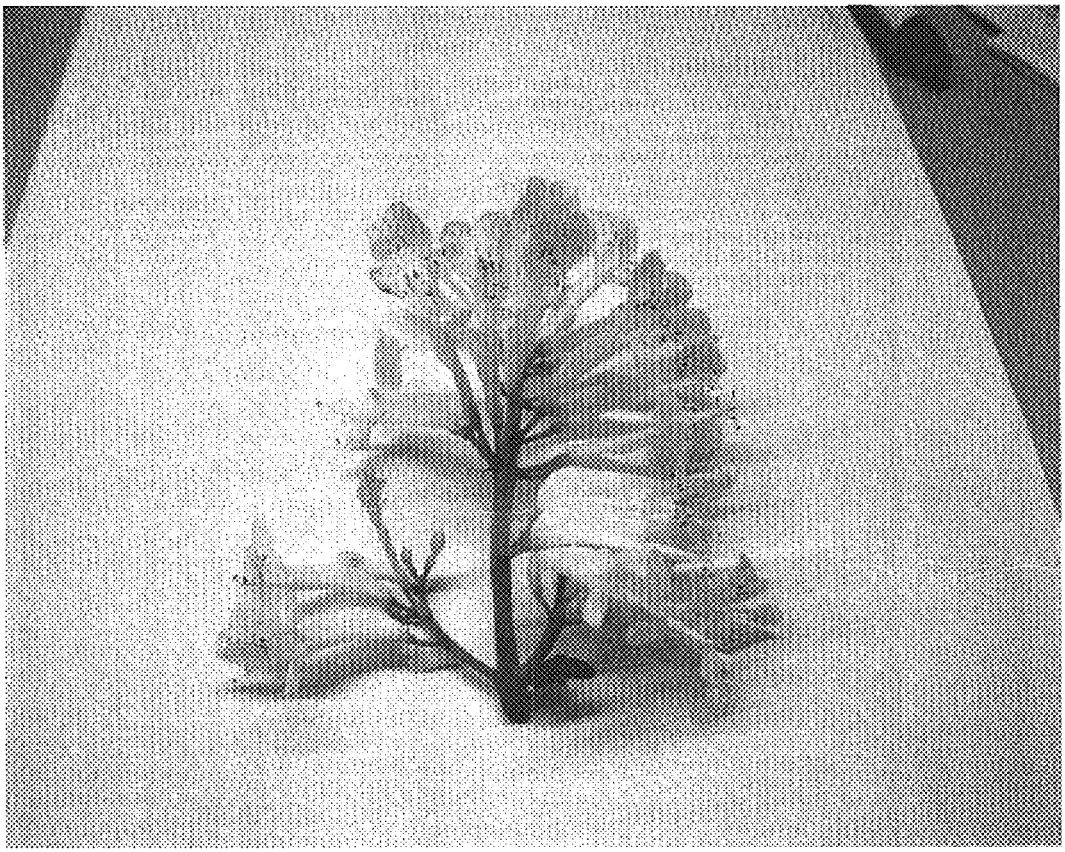

* * * * *